United States Patent [19]

Bader et al.

[11] 4,220,788

[45] Sep. 2, 1980

[54] PROCESS FOR THE PREPARATION OF 2-ARYL-2H-BENZOTRIAZOLES

[75] Inventors: Rolf Bader, Riehen; Leopold Küng, Pratteln; Peter Waldvogel, Füllinsdorf, all of Switzerland

[73] Assignee: Ciba-Geigy Corporation, Ardsley, N.Y.

[21] Appl. No.: 932,730

[22] Filed: Aug. 10, 1978

[30] Foreign Application Priority Data

Aug. 17, 1977 [CH] Switzerland ............. 10091/77

[51] Int. Cl.² ........................... C07D 249/20
[52] U.S. Cl. ..................... 548/259; 548/260; 548/261
[58] Field of Search ............. 260/308 B; 548/259, 548/260, 261

[56] References Cited

U.S. PATENT DOCUMENTS

| 3,978,074 | 8/1976 | Jancis | 260/308 B |
| 4,001,266 | 1/1977 | Rody et al. | 260/308 B |

OTHER PUBLICATIONS

Imai et al., J. Org. Chem., vol. 42, No. 3 (1977), pp. 431-434.

Primary Examiner—Paul M. Coughlan, Jr.
Attorney, Agent, or Firm—Luther A. R. Hall

[57] ABSTRACT

A process for producing benzotriazoles of the formula I

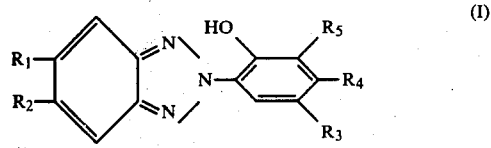

wherein
$R_1$ is hydrogen or chlorine,
$R_2$ is hydrogen, chlorine, $C_1-C_4$ alkyl, $C_1-C_4$ alkoxy, $C_2-C_9$ alkoxycarbonyl, carboxyl or sulfo,
$R_3$ is $C_1-C_{12}$ alkyl, $C_1-C_4$ alkoxy, phenyl, ($C_1-C_8$ alkyl)-phenyl, $C_5-C_6$ cycloalkyl, $C_2-C_9$ alkoxycarbonyl, chlorine, carboxyethyl or $C_7-C_9$ phenylalkyl,
$R_4$ is hydrogen, $C_1-C_4$ alkyl, $C_1-C_4$ alkoxy, chlorine or hydroxyl, and
$R_5$ is hydrogen, $C_1-C_{12}$ alkyl, chlorine, $C_5-C_6$ cycloalkyl or $C_7-C_9$ phenylalkyl, which process comprises treating a benzotriazole-N-oxide of the formula II

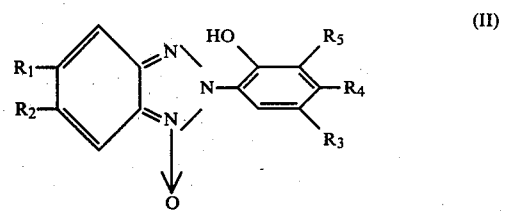

wherein $R_1$, $R_2$, $R_3$, $R_4$ and $R_5$ have the above meanings, at a temperature of 20°–150° C., with an amine; or treating an o-nitroazobenzene of the formula III

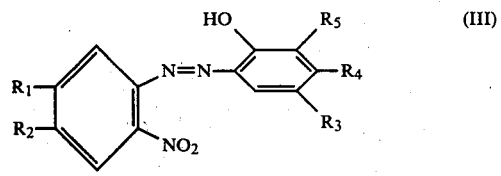

wherein $R_1$, $R_2$, $R_3$, $R_4$ and $R_5$ have the above meanings, at a temperature of 20°–150° C., with an amine.

29 Claims, No Drawings

PROCESS FOR THE PREPARATION OF 2-ARYL-2H-BENZOTRIAZOLES

The invention relates to a novel process for producing benzotriazoles from benzotriazole-N-oxides or from o-nitroazobenzenes.

Benzotriazoles are known, and commercially obtainable, additives for polymers, particularly light stabilisers or oil additives (see for example U.S. Pat. No. 3,004,896), which have been produced hitherto by reduction of o-nitroazobenzenes with zinc in alcoholic sodium hydroxide solution (for example U.S. Pat. No. 3,072,585), with sulfides or zinc/hydrochloric acid (for example U.S. Pat. No. 2,362,988), by means of electrolysis (Chem. Abstr. 24, 2060 (1930)), with hydrazine (U.S. Pat. No. 4,001,266), or by means of catalytic hydrogenation (U.S. Pat. No. 3,978,074). These known processes are however attended with environmental contamination and waste-water problems, and lead as a result of reduction reactions to cleavage products and, in some cases, to dehalogenation phenomena, and give in part inadequate yields and products of impure quality.

In order to convert nitrobenzenes into aminobenzenes, there is known a hydrogen-transfer system consisting of a soluble noble-metal-salt catalyst, for example ruthenium chloride, and an amine as hydrogen donor, such as indoline (Imai et al., J. Org. Chem., 1977, 431–434, Vol. 42). The amines are selected according to their suitability as hydrogen donors, and in this respect particularly indoline and also tetrahydroquinoline, which readily convert as a result of dehydrogenation into stable aromatic compounds, are outstanding, whereas aliphatic amines, such as n-propylamine, tri-n-propylamine, tri-n-octylamine or cyclohexylamine, or alternatively N,N-dimethylaniline, indan and pyridine, have virtually no hydrogen-donorproperties and are described as being poor or completely unsuitable hydrogen-donors. Azobenzenes and hydrazobenzenes are cleaved by hydrogenation to the corresponding aminobenzenes under conditions identical to those for nitrobenzenes.

Starting from this prior art, the present invention teaches that specifically substituted nitrobenzenes, namely o-nitroazobenzenes or benzotriazole-N-oxides which are obtainable therefrom, can be deoxygenated by cyclisation with amines *without* a metal-salt catalyst, and particularly with those amines which are unsuitable or only moderately suitable for the known catalytic hydrogen-transfer mentioned above. It could not have been anticipated that in the process according to the invention there would be obtained with amines, which are stated to be unsuitable or only moderately suitable for the catalytic hydrogen-transfer in the case of nitrobenzene, better yields than those described for aminobenzene, and what is more better yields without the use of a catalyst. Furthermore, it could not have been anticipated that with the reduction of the o-nitroazobenzenes according to the invention there would not occur a cleavage by hydrogenation like that occurring in the case of azobenzene and hydrazobenzene. The surprising feature is not only the fact that the presence of a metal compound is optional, but in particular also the fact that even in the presence of metal compounds the known cleavage by reduction of o-nitroazobenzenes to aminobenzenes does not occur. Also the reduction according to the invention of benzotriazole-N-oxides could not have been deduced from the prior art and yet is surprisingly quite possible.

Accordingly, the invention relates to a process for producing benzotriazoles of the formula I

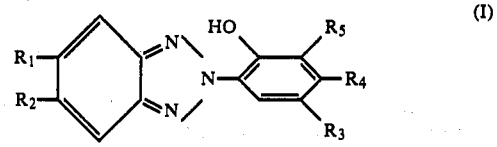

wherein
$R_1$ is hydrogen or chlorine,
$R_2$ is hydrogen, chlorine, $C_1$–$C_4$ alkyl, $C_1$–$C_4$ alkoxy, $C_2$–$C_9$ alkoxycarbonyl, carboxyl or sulfo,
$R_3$ is $C_1$–$C_{12}$ alkyl, $C_1$–$C_4$ alkoxy, phenyl, ($C_1$–$C_8$ alkyl)-phenyl, $C_5$–$C_6$ cycloalkyl, $C_2$–$C_9$ alkoxycarbonyl, chlorine, carboxyethyl or $C_7$–$C_9$ phenylalkyl,
$R_4$ is hydrogen, $C_1$–$C_4$ alkyl, $C_1$–$C_4$ alkoxy, chlorine or hydroxyl, and
$R_5$ is hydrogen, $C_1$–$C_{12}$ alkyl, chlorine, $C_5$–$C_6$ cycloalkyl or $C_7$–$C_9$ phenylalkyl,
which process comprises treating a benzotriazole-N-oxide of the formula II

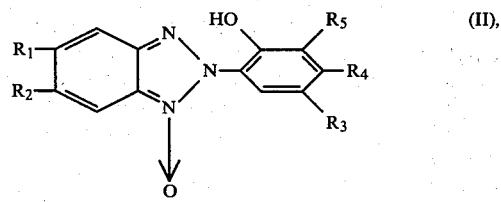

wherein $R_1$, $R_2$, $R_3$, $R_4$ and $R_5$ have the above meanings, at a temperature of 20°–150° C., with an amine; or treating a benzotriazole-N-oxide of the formula II formed in situ, which is formed by treating an o-nitroazobenzene of the formula III

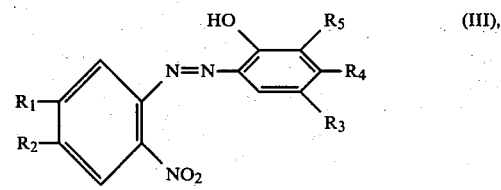

wherein $R_1$, $R_2$, $R_3$, $R_4$ and $R_5$ have the above meanings, at a temperature of 20°–150° C. with an amine.

As $C_1$–$C_4$ alkyl, $R_2$ is for example ethyl, n-butyl or in particular methyl, as $C_1$–$C_4$ alkoxy, $R_2$ is for example ethoxy, n-butoxy or especially methoxy, and as $C_2$–$C_9$ alkoxycarbonyl, $R_2$ is for example ethoxycarbonyl, n-octoxycarbonyl or particularly methoxycarbonyl.

As $C_1$–$C_{12}$ alkyl, $R_3$ is for example ethyl, amyl, tert-octyl, n-dodecyl or especially methyl or tert-butyl, as $C_1$–$C_4$ alkoxy, $R_3$ is for example ethoxy, n-butoxy or in particular methoxy, as ($C_1$–$C_8$ alkyl)-phenyl, $R_3$ is for example methylphenyl, tert-butylphenyl, tert-amylphenyl or tert-octylphenyl, as $C_5$–$C_6$ cycloalkyl, $R_3$ is for example cyclopentyl or especially cyclohexyl, as $C_2$–$C_9$ alkoxycarbonyl, $R_3$ is for example ethoxycarbonyl, n-octoxycarbonyl or particularly methoxycarbonyl, and as $C_7$–$C_9$ phenylalkyl, $R_3$ is for example α-methylbenzyl, αα-dimethylbenzyl or benzyl.

As $C_1$–$C_4$ alkyl, $R_4$ is for example ethyl, n-butyl or especially methyl, and as $C_1$–$C_4$ alkoxy, $R_4$ is for example ethoxy, n-butoxy or in particular methoxy.

As $C_1$–$C_{12}$ alkyl, $R_5$ is for example sec-butyl, tert-amyl, tert-octyl, n-dodecyl or especially methyl or tert-butyl, as $C_5$–$C_6$ cycloalkyl, $R_5$ is for example cyclopentyl or particularly cyclohexyl, and as $C_7$–$C_9$ phenylalkyl, $R_5$ is for example α-methylbenzyl, α,α-dimethylbenzyl or benzyl.

Preferably, $R_1$ is hydrogen, $R_2$ is hydrogen, chlorine, methyl, ethyl, methoxyl methoxy or carboxyl, $R_3$ is $C_1$–$C_{12}$ alkyl, cyclohexyl, phenyl, chlorine, α-methylbenzyl or carboxyethyl, $R_4$ is hydrogen, methyl or hydroxyl, and $R_5$ is hydrogen, chlorine, $C_1$–$C_{12}$ alkyl, cyclohexyl, benzyl or α-methylbenzyl.

Particularly preferably, $R_1$ is hydrogen, $R_2$ is hydrogen or chlorine, $R_3$ is methyl, tert-butyl, tert-amyl, tert-octyl, sec-butyl, cyclohexyl, chlorine or carboxyethyl, $R_4$ is hydrogen, and $R_5$ is hydrogen, chlorine, methyl, sec-butyl, tert-butyl, tert-amyl, tert-octyl or α-methylbenzyl.

Suitable for the process according to the invention are preferably relatively strong basically reacting amines, especially primary or secondary amines, but above all primary amines. Primary amines are for example alkylamines such as $C_1$–$C_{18}$ alkylamines, for example propylamine, aryl amines such as $C_6$–$C_{20}$ arylamines, for example 2,6-dimethylaniline or 2-methyl-6-ethyl-aniline, cycloalkylamines such as $C_5$–$C_8$ cycloalkylamines, for example cyclohexylamine, or alkylenediamines such as $C_2$–$C_{18}$ alkylene diamines, for example trimethylenediamine. Secondary amines are for example dialkylamines such as $C_2$–$C_{36}$ dialkylamines, for example dipropylamine, N-aryl-N-alkyl-amines such as $C_6$–$C_{10}$ N-aryl-($C_1$–$C_{18}$)-N-alkyl-amines, for example N-methylaniline, or N-cycloalkyl-N-alkylamines such as $C_5$–$C_8$ N-cycloalkyl-($C_1$–$C_{18}$)-N-alkylamines, for example N-methyl-cyclohexylamine, or secondary amines having primary groups in the same molecule, such as $H_2N$—$(CH_2)_n$—$NH$—$(CH_2)_m$—$NH_2$ with n and m independently of one another being 2–6, for example 3,3-diamino-dipropylamine, or pyrrolidine, piperidine, piperazine or morpholine. The primary amines and among these the alkylamines and alkylenediamines are especially preferred. Also mixtures of amines, particularly of the above amines, can advantageously be used.

The amine is used preferably in amounts of 3 to 10 mols per mol of o-nitroazobenzene or N-oxide compound. The amine can either be present from the beginning in the reaction mixture, or be added during the course of the reaction.

The temperature in the process according to the invention is about 20°–150° C., especially 50°–120° C., and in particular 80°–120° C., and depends in the individual case on the reactants chosen, on the solvent optionally used, and on the reaction vessel. For the purpose of the exclusion of air, an inert-gas atmosphere, such as of nitrogen or rare gases, is advantageous. If the process is performed at temperatures above the boiling point of the amine and/or solvent used, a closed system is advisable so that the reaction can be performed under pressure.

In a suitable method of performing the process there is used a solvent, whereby the amine can concomitantly take over the role of solvent. Depending on the choice of solvent, the reaction can be performed in one phase or in two phases; in one phase for example if the amine acts as solvent or if inert organic solvents are used such as hydrocarbons, for example aliphatic, cycloaliphatic or aromatic hydrocarbons, such as hexane, heptane, cyclohexane, benzene, toluene or xylene, or mixtures thereof, or polar inert organic solvents such as alcohols, for example alkanols such as methanol, ethanol, isopropanol, n-propanol, n-butanol or 2-methoxyethanol, or ethers such as tetrahydrofuran, dioxane or 1,2-dimethoxyethane or trialkyl phosphates such as tributyl phosphate, or alternatively amides such as dialkylformamide, for example dimethylformamide or dimethylacetamide. In two phases the reaction is performed preferably in an aqueous/organic solvent, such as water/hydrocarbon, as above, in which case the processing of the reaction mixture is particularly advantageous.

It is advantageous for obtaining a good yield in the process according to the invention if the o-nitroazobenzene, either dissolved in a solvent or undiluted, is fed in controlled amounts into the reaction vessel during the reaction.

Likewise advantageous for achieving a good yield, especially however for shortening the reaction time, has proved the addition of catalysts. These are metals and metal compounds from the groups IB, IIB, VB, VIB, VIIB and VIII of the periodic system, particularly metals of the groups IB, VB, VIB and VIII, such as Cu, Ag, Au, V, Cr, Mo, W, Fe, Ru, Os, Co, Rh, Ir, Ni, Pd and Pt. Economically advantageous metals such as Fe, Co, Ni and more especially Cu are particularly preferred.

If is of advantage to use the metals in the form of soluble compounds, such as salts or complexes. Salts of weak organic acids, for example acetates or propionates, are preferred. Also suitable however are salts of inorganic acids, for example carbonates, or basic salts of inorganic acids, for example hydroxycarbonates. It is also possible to use oxides or hydroxides of these metals. The metals can also be used as complexes, such as acetylacetonates or salicylaldiminates. Acetylacetonates are preferred. Moreover, suitable solvents can form with metal salts complexes in situ, which act as suitable catalysts. Preferably, the catalyst, such as the metal salt, is used in an amount less than the stoichiometric amount, particularly in amounts of 1 to 25 mol %, relative to the o-nitroazobenzene or N-oxide compound.

The advantages of the process are that it produces high yields of pure product, that undesirable by-products are to a great extent avoided, and that problems connected with waste-water and exhaust gases are largely eliminated. There is also the advantage that, compared with a catalytic hydrogenation, dehalogenation need not give rise to concern. If a cresol occurs as by-product, this can be advantageously separated and again used for producing o-nitroazobenzene (formula III) or the N-oxide (formula II); it is therefore not lost to the reaction cycle. Furthermore, gaseous reducing agents are not necessary, and the reaction medium, particularly in the case of the two-phase procedure, can be utilised again.

The process according to the invention is likewise suitable as a process for producing benzotriazole-N-oxides of the formula II; this process comprises treating an o-nitroazobenzene of the formula III

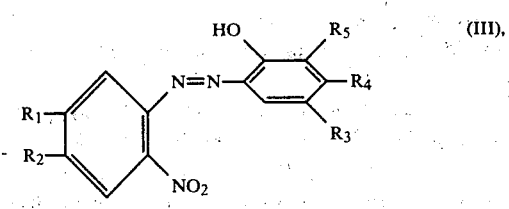

wherein $R_1$, $R_2$, $R_3$, $R_4$ and $R_5$ have the above meanings, at a temperature of 20°–150° C., with an amine.

This reaction is performed in detail, and in its preferred embodiments in particular, in the manner described above for the production of benzotriazoles. The optionally isolated N-oxide can be advantageously used, optionally without purification, as starting material in the process described in the foregoing, or alternatively this process can yield the desired benzotriazole (formula I) directly from the o-nitroazobenzene (formula III), without the necessity of isolating the N-oxide of the formula II. In order to obtain an N-oxide of the formula II, the reaction is accordingly prematurely terminated, with in particular a shorter reaction time being used.

The starting materials are known, especially from the prior art cited, or in cases where they are novel they can be produced by methods analogous to known methods.

The invention is further illustrated in the following by means of Examples which in no way limit the scope of the invention.

EXAMPLE 1

10 g of 2-nitro-2'-hydroxy-5'-methyl-azobenzene (0.04 mol) in 150 ml of 1,3-diaminopropane is heated for 20 hours at 85°–90° C. with the exclusion of air.

The 1,3-diaminopropane is distilled off and the resulting distillation residue is analysed. It consists to the extent of 40% of theory of 2-(2'-hydroxy-5'-methylphenyl)-benzotriazole. p-Cresol as by-product is present to the extent of 34% of theory.

The reduction can be performed in an analogous manner with the following amines to give analogous results:
ethylenediamine,
3,3'-diaminodipropylamine,
1,6-diaminohexane,
cyclohexylamine,
benzylamine,
diethylamine,
piperidine,
morpholine, and
triethylamine.

EXAMPLE 2

11.6 g of 1,3-diaminopropane (0.16 mol) and 2 g of copper-II-acetate (0.01 mol) are placed into 50 ml of water and the whole is heated, with the exclusion of air and with stirring, to 85°–90° C. A solution of 10 g of 2-nitro-2'-hydroxy-5'-methyl-azobenzene (0.04 mol) in 100 ml of xylene heated to 60° C. is then added, and after 20 hours the reaction mixture is cooled to room temperature. The aqueous phase is separated, and the organic phase is extracted with aqueous hydrochloric acid, and then washed with water until neutral. The xylene is distilled off to leave 7.7 g of crude product. Analysis of the crude product by means of LC (liquid chromatography) gives 86% of theory of 2-(2'-hydroxy-5'-methylphenyl)-benzotriazole.

The aqueous phase containing the copper salt and the amine can be used for a further reaction after the two components have been replenished to give the initial values.

EXAMPLE 3

The process is carried out according to Example 2 except that 9.4 g of 2-(2'-hydroxy-5'-methylphenyl)-benzotriazole-N-oxide is used instead of 2-nitro-2'-hydroxy-5'-methyl-azobenzene. There is obtained 8.5 g of crude product, and the LC analysis of this gives 92.4% of theory of 2-(2'-hydroxy-5'-methylphenyl)-benzotriazole.

EXAMPLE 4

22.6 g of piperidine (0.32 mol) and 2.62 g of copper-II-acetylacetonate (0.01 mol) are placed into 50 ml of water, and the whole is heated to 85°–90° C. with the exclusion of air. A solution of 10 g of 2-nitro-2'-hydroxy-5'-methylazobenzene (0.04 mol) in 100 ml of xylene heated to 60° C. is then added, and the reaction is finished after 6 hours. Processing according to Example 2 yields 8.37 g of crude product. The yield of 2-(2'-hydroxy-5'-methylphenyl)-benzotriazole is 70%.

EXAMPLE 5

The procedure is carried out according to Example 2 with the exception that copper-II-hydroxycarbonate is used in place of Cu-II-acetate. The yield is 64% of 2-(2'-hydroxy-5'-methylphenyl)-benzotriazole.

EXAMPLE 6

11.6 g of 1,3-diaminopropane (0.16 mol) and 2.62 g of Cu-II-acetylacetonate are placed into 100 ml of dimethylformamide, and the whole is heated in an inert atmosphere to 100° C. A solution of 10 g of 2-nitro-2'-hydroxy-5'-methyl-azobenzene in 50 ml of dimethylformamide is then added, and after 3 hours the reaction is finished. The conversion to 2-(2'-hydroxy-5'-methylphenyl)-benzotriazole gives a yield of 64%.

EXAMPLE 7

11.6 g of 1,3-diaminopropane (0.16 mol) and 2.0 g of Cu-II-acetate are dissolved in 100 ml of methyl cellosolve and the solution is heated to 95° C. with the exclusion of air. A solution of 10 g of 2-nitro-2'-hydroxy-5'-methyl-azobenzene in 100 ml of methyl cellosolve heated to 60° C. is then continuously added dropwise during 8 hours, and the mixture is subsequently allowed to react for 2 hours. The volatile constituents of the reaction mixture are removed by vacuum distillation, and the distillation residue is taken up in toluene. The toluene solution is extracted with aqueous hydrochloric acid, and washed neutral with water. The toluene is distilled off to leave 8.31 g of crude product containing 96.5% of 2-(2'-hydroxy-5'-methylphenyl)-benzotriazole. The conversion to 2-(2'-hydroxy-5'-methylphenyl)-benzotriazole gives a yield of 92.3%.

EXAMPLE 8

2-Nitro-4-chloro-2'-hydroxy-3'-tert.-butyl-5'-methyl-azobenzene is reacted, according to Example 2, with Cu-II-acetylacetonate to give 2-(2'-hydroxy-3'-tert.-butyl-5'-methyl-phenyl)-5-chlorobenzotriazole; the yield is 70% of theory.

EXAMPLE 9

2-Nitro-4-chloro-2'-hydroxy-3',5'-di-tert.-butyl-azobenzene is reacted, according to Example 8, to give 2-(2'-hydroxy-3',5'-di-tert.-butyl-phenyl)-5-chlorobenzotriazole in a yield of 75% of theory.

EXAMPLE 10

2-Nitro-2'-hydroxy-3',5'-di-tert.-butyl-azobenzene is reacted, according to Example 8, to give 2-(2'-hydroxy-3',5'-di-tert.-butyl-phenyl)-benzotriazole in a yield of 70% of theory.

EXAMPLE 11

2-Nitro-2'-hydroxy-3',5'-di-tert.-pentyl-azobenzene is reacted, according to Example 8, to give 2-(2'-hydroxy-3',5'-di-tert.-pentyl-phenyl)-benzotriazole in a yield of 85% of theory. We claim:

1. A process for producing a benzotriazole of the formula I

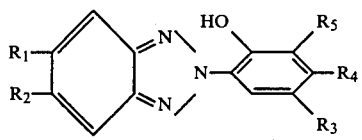

wherein
$R_1$ is hydrogen or chlorine,
$R_2$ is hydrogen, chlorine, $C_1$–$C_4$ alkyl, $C_1$–$C_4$ alkoxy, $C_2$–$C_9$ alkoxycarbonyl, carboxyl or sulfo,
$R_3$ is $C_1$–$C_{12}$ alkyl, $C_1$–$C_4$ alkoxy, phenyl, ($C_1$–$C_8$ alkyl)-phenyl, $C_5$–$C_6$ cycloalkyl, $C_2$–$C_9$ alkoxycarbonyl, chlorine, carboxyethyl or $C_7$–$C_9$ phenylalkyl,
$R_4$ is hydrogen, $C_1$–$C_4$ alkyl, $C_1$–$C_4$ alkoxy, chlorine or hydroxyl, and
$R_5$ is hydrogen, $C_1$–$C_{12}$ alkyl, chlorine, $C_5$–$C_6$ cycloalkyl or $C_7$–$C_9$ phenylalkyl,
which process consists essentially of treating a benzotriazole-N-oxide of the formula II

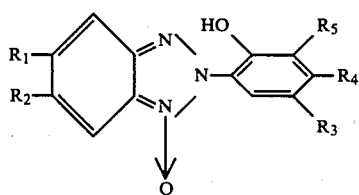

wherein
$R_1$, $R_2$, $R_3$, $R_4$ and $R_5$ have the above meanings, at a temperature of 20°–150° C., with an amine which is an alkylamine of 1 to 18 carbon atoms, an arylamine of 6 to 20 carbon atoms, a cycloalkylamine of 5 to 8 carbon atoms, an alkylenediamine of 2 to 18 carbon atoms, a dialkylamine of 2 to 36 carbon atoms, an N-aryl-N-alkylamine of 6 to 10 carbon atoms in the aryl group and 1 to 18 carbon atoms in the alkyl group, an N-cycloalkyl-N-alkylamine of 5 to 8 carbon atoms in the cycloalkyl group and 1 to 18 carbon atoms in the alkyl group, an amine of the formula

$NH_2$—$(CH_2)_n$—$NH$—$(CH_2)_m$—$NH_2$ where n and m independently are 2 to 6; pyrrolidine, piperidine, piperazine or morpholine; or mixtures thereof.

2. A process according to claim 1, wherein $R_1$ is hydrogen, $R_2$ is hydrogen, chlorine, methyl, ethyl, methoxy or carboxyl, $R_3$ is $C_1$–$C_{12}$ alkyl, cyclohexyl, phenyl, chlorine, α-methylbenzyl or carboxyethyl, $R_4$ is hydrogen, methyl or hydroxyl, and $R_5$ is hydrogen, chlorine, $C_1$–$C_{12}$ alkyl, cyclohexyl, benzyl or α-methylbenzyl.

3. A process according to claim 1, wherein $R_1$ is hydrogen, $R_2$ is hydrogen or chlorine, $R_3$ is methyl, tert-butyl, tert-amyl, tert-octyl, sec-butyl, cyclohexyl, chlorine or carboxyethyl, $R_4$ is hydrogen, and $R_5$ is hydrogen, chlorine, methyl, sec-butyl, tert-butyl, tert-amyl, tert-octyl or α-methylbenzyl.

4. A process according to claim 1, wherein the treatment is performed at 50°–120° C.

5. A process according to claim 1, wherein an inert solvent is used.

6. A process according to claim 1, wherein the reaction is performed in the presence of a metal catalyst or metal-compound catalyst.

7. A process according to claim 6, wherein the metal, or the metal of the metal compound, comes from the groups IB, IIB, VB, VIB, VIIB or VIII of the periodic system.

8. A process according to claim 6, wherein the metal or the metal compound contains copper as the metal.

9. A process according to claim 1 wherein the amine is an alkylamine or alkylenediamine.

10. A process according to claim 4 which is performed at 80°–120° C.

11. A process for producing a benzotriazole-N-oxide of the formula II

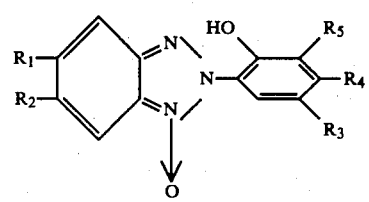

wherein
$R_1$ is hydrogen or chlorine,
$R_2$ is hydrogen, chlorine, $C_1$–$C_4$ alkyl, $C_1$–$C_4$ alkoxy, $C_2$–$C_9$ alkoxycarbonyl, carboxyl or sulfo,
$R_3$ is $C_1$–$C_{12}$ alkyl, $C_1$–$C_4$ alkoxy, phenyl, ($C_1$–$C_8$-alkyl)-phenyl, $C_5$–$C_6$ cycloalkyl, $C_2$–$C_9$ alkoxycarbonyl, chlorine, carboxyethyl or $C_7$–$C_9$ phenylalkyl,
$R_4$ is hydrogen, $C_1$–$C_4$ alkyl, $C_1$–$C_4$ alkoxy, chlorine or hydroxyl, and
$R_5$ is hydrogen, $C_1$–$C_{12}$ alkyl, chlorine, $C_5$–$C_6$ cycloalkyl or $C_7$–$C_9$ phenylalkyl,
which process consists essentially of treating an o-nitroazobenzene of the formula III

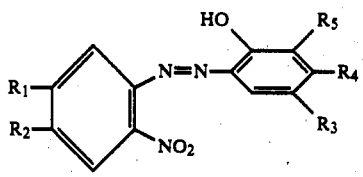

wherein

R₁, R₂, R₃, R₄ and R₅ have the above meanings, at a temperature of 20°–150° C. with an amine which is an alkylamine of 1 to 18 carbon atoms, an arylamine of 6 to 20 carbon atoms, a cycloalkylamine of 5 to 8 carbon atoms, an alkylene diamine of 2 to 18 carbon atoms, a dialkylamine of 2 to 36 carbon atoms, an N-aryl-N-alkylamine of 6 to 10 carbon atoms in the aryl group and 1 to 18 carbon atoms in the alkyl group, an N-cycloalkyl-N-alkylamine of 5 to 8 carbon atoms in the cycloalkyl group and 1 to 18 carbon atoms in the alkyl group, an amine of the formula $$NH_2-(CH_2)_n-NH-(CH_2)_m-NH_2$$

where n and m independently are 2 to 6; pyrrolidine, piperidine, piperazine or morpholine; or mixtures thereof; and isolating the N-oxide before further reaction thereof.

12. A process according to claim 11, wherein $R_1$ is hydrogen, $R_2$ is hydrogen, chlorine, methyl, ethyl, methoxy or carboxyl, $R_3$ is $C_1$–$C_{12}$ alkyl, cyclohexyl, phenyl, chlorine, α-methylbenzyl or carboxyethyl, $R_4$ is hydrogen, methyl or hydroxyl, and $R_5$ is hydrogen, chlorine, $C_1$–$C_{12}$ alkyl, cyclohexyl, benzyl or α-methylbenzyl.

13. A process according to claim 11, wherein $R_1$ is hydrogen, $R_2$ is hydrogen or chlorine, $R_3$ is methyl, tert-butyl, tert-amyl, tert-octyl, sec-butyl, cyclohexyl, chlorine or carboxyethyl, $R_4$ is hydrogen, and $R_5$ is hydrogen, chlorine, methyl, sec-butyl, tert-butyl, tert-amyl, tert-octyl or α-methylbenzyl.

14. A process according to claim 11, wherein the treatment is performed at 50°–120° C.

15. A process according to claim 11, wherein an inert solvent is used.

16. A process according to claim 11, wherein the reaction is performed in the presence of a metal catalyst or metal-compound catalyst.

17. A process according to claim 16, wherein the metal, or the metal of the metal compound, comes from the groups IB, IIB, VB, VIB, VIIB or VIII of the periodic system.

18. A process according to claim 16, wherein the metal or the metal compound contains copper as the metal.

19. A process according to claim 11 wherein the amine is an alkylamine or alkylenediamine.

20. A process for producing a benzotriazole of the formula I

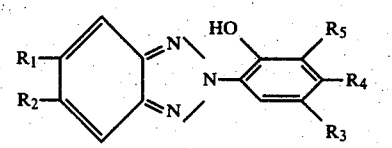

wherein

R₁ is hydrogen or chlorine,

R₂ is hydrogen, chlorine, $C_1$–$C_4$ alkyl, $C_1$–$C_4$ alkoxy, $C_2$–$C_9$ alkoxycarbonyl, carboxyl or sulfo, R₃ is $C_1$–$C_{12}$ alkyl, $C_1$–$C_4$ alkoxy, phenyl, ($C_1$–$C_8$ alkyl)-phenyl, $C_5$–$C_6$ cycloalkyl, $C_2$–$C_9$ alkoxycarbonyl, chlorine, carboxyethyl or $C_7$–$C_9$ phenylalkyl, R₄ is hydrogen, $C_1$–$C_4$ alkyl, $C_1$–$C_4$ alkoxy, chlorine or hydroxyl, and R₅ is hydrogen, $C_1$–$C_{12}$ alkyl, chlorine, $C_5$–$C_6$ cycloalkyl or $C_7$–$C_9$ phenylalkyl, which consists essentially of treating an o-nitroazobenzene of the formula III

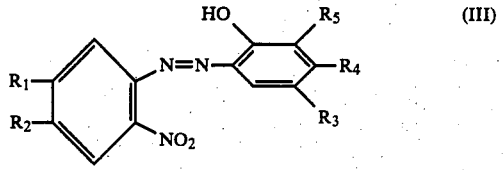

wherein

R₁, R₂, R₃, R₄ and R₅ have the above meanings, at a temperature of 20°–150° C., with an amine which is an alkylamine of 1 to 18 carbon atoms, an arylamine of 6 to 20 carbon atoms, a cycloalkylamine of 5 to 8 carbon atoms, an alkylenediamine of 2 to 18 carbon atoms, a dialkylamine of 2 to 36 carbon atoms, an N-aryl-N-alkylamine of 6 to 10 carbon atoms in the aryl group and 1 to 18 carbon atoms in the alkyl group, an N-cycloalkyl-N-alkylamine of 5 to 8 carbon atoms in the cycloalkyl group and 1 to 18 carbon atoms in the alkyl group, an amine of the formula $$NH_2-(CH_2)_n-NH-(CH_2)_m-NH_2$$

where n and m independently are 2 to 6; pyrrolidine, piperidine, piperazine or morpholine; or mixtures thereof.

21. A process according to claim 20, wherein $R_1$ is hydrogen, $R_2$ is hydrogen, chlorine, methyl, ethyl, methoxy or carboxyl, $R_3$ is $C_1$–$C_{12}$ alkyl, cyclohexyl, phenyl, chlorine, α-methylbenzyl or carboxyethyl, $R_4$ is hydrogen, methyl or hydroxyl, and $R_5$ is hydrogen, chlorine, $C_1$–$C_{12}$ alkyl, cyclohexyl, benzyl or α-methylbenzyl.

22. A process according to claim 20, wherein $R_1$ is hydrogen, $R_2$ is hydrogen or chlorine, $R_3$ is methyl, tert-butyl, tert-amyl, tert-octyl, sec-butyl, cyclohexyl, chlorine or carboxyethyl, $R_4$ is hydrogen, and $R_5$ is hydrogen, chlorine, methyl, sec-butyl, tert-butyl, tert-amyl, tert-octyl or α-methylbenzyl.

23. A process according to claim 20, wherein the treatment is performed at 50°–120° C.

24. A process according to claim 20, wherein an inert solvent is used.

25. A process according to claim 20, wherein the reaction is performed in the presence of a metal catalyst or metal-compound catalyst.

26. A process according to claim 25, wherein the metal, or the metal of the metal compound, comes from the groups IB, IIB, VB, VIB, VIIB or VIII of the periodic system.

27. A process according to claim 25, wherein the metal or the metal compound contains copper as the metal.

28. A process according to claim 20 wherein the amine is an alkylamine or alkylenediamine.

29. A process according to claim 23 which is performed at 80°–120° C.

* * * * *